(12) United States Patent
Oren et al.

(10) Patent No.: US 7,883,519 B2
(45) Date of Patent: Feb. 8, 2011

(54) SUTURE MANIPULATING INSTRUMENT PARTICULARLY USEFUL WITH ENDOSCOPES

(76) Inventors: Ran Oren, Kibbutz Gaaton, 25130 Doar Na Oshrat (IL); Dan Moor, Kibbutz Gaaton, 25130 Doar Na Oshrat (IL)

( * ) Notice: Subject to any disclaimer, the term of this patent is extended or adjusted under 35 U.S.C. 154(b) by 548 days.

(21) Appl. No.: 10/984,851

(22) Filed: Nov. 10, 2004

(65) Prior Publication Data

US 2006/0009791 A1    Jan. 12, 2006

Related U.S. Application Data

(60) Provisional application No. 60/585,079, filed on Jul. 6, 2004.

(51) Int. Cl.
*A61B 17/28* (2006.01)
(52) U.S. Cl. .................... 606/148; 606/207
(58) Field of Classification Search .............. 606/144, 606/148, 207, 205
See application file for complete search history.

(56) References Cited

U.S. PATENT DOCUMENTS

| | | | |
|---|---|---|---|
| 1,545,682 A | 7/1925 | Nelson | |
| 1,583,271 A | 5/1926 | Biro | |
| 2,738,790 A | 3/1956 | Todt, Sr. et al. | |
| 2,959,172 A | 11/1960 | Held | |
| 3,877,434 A | 4/1975 | Ferguson et al. | |
| 4,372,302 A | 2/1983 | Åkerlund | |
| 4,602,635 A | 7/1986 | Mulhollan et al. | |
| 4,641,652 A | 2/1987 | Hutterer et al. | |
| 4,643,190 A | 2/1987 | Heimberger | |
| 4,741,330 A | 5/1988 | Hayhurst | |
| 4,779,616 A | 10/1988 | Johnson | |
| 4,781,190 A | 11/1988 | Lee | |
| 4,890,615 A | 1/1990 | Caspari et al. | |
| 4,923,461 A | 5/1990 | Caspari et al. | |

(Continued)

FOREIGN PATENT DOCUMENTS

WO    WO 02/43558    6/2002

OTHER PUBLICATIONS

Esser "Arthroscopic Meniscus Repair: The Easy Way".Journal of Arthroscopy,9(2): 231-233, 1993.

*Primary Examiner*—Anhtuan T Nguyen
*Assistant Examiner*—Ryan J Severson

(57) ABSTRACT

A suture manipulating instrument, includes: first and second handles manually movable relative to each other to open and closed positions; an elongated shaft having a proximal end fixed to the first handle, and a distal end defining a first jaw engageable with a suture to be manipulated; a second jaw movably mounted to the distal end of the elongated shaft to open and closed positions with respect to the first jaw; and a coupling between the second handle and the second jaw for moving the second jaw to its open and closed positions with respect to the first jaw upon movement of the second handle to open and closed positions with respect to the first handle. The first and second jaws are formed with confronting surfaces configured to firmly grasp a suture between them in the closed position of the second jaw with respect to the first jaw. The distal end of the first jaw is outwardly curved away from the axis of the shaft and is tapered towards its distal tip such as to define a piercing tip for piercing tissue by rotating the elongated shaft about its axis.

20 Claims, 2 Drawing Sheets

U.S. PATENT DOCUMENTS

| | | |
|---|---|---|
| 5,015,250 A | 5/1991 | Foster |
| 5,037,422 A | 8/1991 | Hayhurst et al. |
| 5,041,129 A | 8/1991 | Hayhurst et al. |
| 5,149,329 A | 9/1992 | Richardson |
| 5,176,700 A | 1/1993 | Brown et al. |
| 5,181,919 A | 1/1993 | Bergman et al. |
| 5,201,741 A | 4/1993 | Dulebohn |
| 5,222,508 A | 6/1993 | Contarini |
| 5,222,977 A | 6/1993 | Esser |
| 5,224,946 A | 7/1993 | Hayhurst et al. |
| 5,234,443 A | 8/1993 | Phan et al. |
| 5,236,445 A | 8/1993 | Hayhurst et al. |
| 5,250,054 A | 10/1993 | Li |
| 5,269,809 A | 12/1993 | Hayhurst et al. |
| 5,306,301 A | 4/1994 | Graf et al. |
| 5,312,422 A | 5/1994 | Trott |
| 5,342,389 A | 8/1994 | Haber et al. |
| 5,405,354 A | 4/1995 | Sarrett |
| 5,417,691 A | 5/1995 | Hayhurst |
| 5,474,565 A | 12/1995 | Trott |
| 5,496,335 A * | 3/1996 | Thomason et al. ........... 606/148 |
| 5,499,991 A | 3/1996 | Garman et al. |
| 5,501,692 A | 3/1996 | Riza |
| 5,507,756 A * | 4/1996 | Hasson ....................... 606/139 |
| 5,507,758 A | 4/1996 | Thomason et al. |
| 5,562,683 A | 10/1996 | Chan |
| 5,562,685 A * | 10/1996 | Mollenauer et al. ......... 606/144 |
| 5,601,557 A | 2/1997 | Hayhurst |
| 5,601,578 A | 2/1997 | Murphy |
| 5,618,290 A | 4/1997 | Toy et al. |
| 5,645,588 A | 7/1997 | Graf et al. |
| 5,647,874 A | 7/1997 | Hayhurst |
| 5,713,908 A | 2/1998 | Jameel et al. |
| 5,735,873 A * | 4/1998 | MacLean .................... 606/205 |
| 5,827,299 A * | 10/1998 | Thomason et al. .......... 606/148 |
| 5,910,148 A | 6/1999 | Reimels et al. |
| 5,954,734 A | 9/1999 | Thomason et al. |
| 6,004,332 A * | 12/1999 | Yoon et al. .................. 606/144 |
| 6,074,403 A | 6/2000 | Nord |
| 6,511,487 B1 | 1/2003 | Oren et al. |
| 6,517,552 B1 * | 2/2003 | Nord et al. .................. 606/144 |
| 6,723,107 B1 | 4/2004 | Skiba et al. |
| 6,893,448 B2 | 5/2005 | O'Quinn et al. |
| 6,896,686 B2 | 5/2005 | Weber |
| 2004/0073254 A1 | 4/2004 | Wyman et al. |
| 2005/0043748 A1 | 2/2005 | Oren et al. |

* cited by examiner

US 7,883,519 B2

SUTURE MANIPULATING INSTRUMENT PARTICULARLY USEFUL WITH ENDOSCOPES

RELATED APPLICATION

The present application is based on U.S. Provisional Application Ser. No. 60/585,079, filed on Jul. 6, 2004, and claims the priority date of that application.

FIELD AND BACKGROUND OF THE INVENTION

The present application relates to a suture manipulating instrument for use during a surgical operation. The invention is particularly useful with respect to instruments manipulated via endoscopes during minimal invasive surgery, and is therefore described below with respect to such an application.

In minimally invasive surgery all operations must be performed through a narrow opening, the size of which limits the size of the instruments used and the free space available to manipulate them. Various small-size cutting, grasping, debriding and stitching instruments, capable of operating through small portals, have been developed for this purpose.

Internal suturing is necessary in many endoscopic procedures in order to close wounds or to reattach tissue which became detached from its normal position. In many such procedures, a strand of suture is introduced from the outside to the location to be sutured. The suture is then passed through a layer of tissue and retrieved from the exit side. In other cases, a suture attached to an anchoring element must be captured and passed through tissue.

Many suture passing and stitching devices are available to the endoscopist. Examples of such devices are described in U.S. Pat. No. 5,499,991 (Linvatec), and U.S. Pat. No. 5,222,977 (R. D. Esser), and in the publication "Arthroscopic Meniscus Repair": Journal of Arthroscopy Vol. 9, No. 2, p. 231 by R. D. Esser, as well as in Catalogs of Linvatec-Concept Inc., Arthrex Inc. However, all the known devices are limited in the functions capable of being performed, in the direction of approach, or in their maneuverability within the limited space available.

The aim of this invention is to provide a novel design having advantages with respect to one or more of the above-mentioned limitations of existing devices and offering an optimal solution to endoscopic suture management.

BRIEF SUMMARY OF THE PRESENT INVENTION

According to one aspect of the present invention, there is provided a suture manipulating instrument, comprising: first and second handles manually movable relative to each other to open and closed positions;

an elongated shaft having a proximal end fixed to said first handle, and a distal end defining a first jaw engageable with a suture to be manipulated;

a second jaw movably mounted to said distal end of said elongated shaft to open and closed positions with respect to said first jaw; and a coupling between said second handle and said second jaw for moving said second jaw to its open and closed positions with respect to said first jaw upon the movement of said second handle to open and closed positions with respect to said first handle; said first and second jaws being formed with confronting surfaces configured to firmly grasp a suture between them in the closed position of said second jaw with respect to said first jaw; the surface of the distal end of said first jaw opposite to its surface confronting the second jaw being outwardly curved away from the axis of said shaft according to a helical configuration, and being tapered towards its distal tip such as to define a piercing tip facing away from the axis of said shaft, for piercing tissue, and for advancing said piercing tip through the pierced tissue with the suture caught between said confronting surfaces of the closed jaws before or after the tissue is pierced, by rotating said elongated shaft about its axis.

According to further features in the described preferred embodiments, the convex surface of the first jaw and the confronting surface of the second jaw define, in the closed position of the jaws, an eyelet for receiving a suture; the eyelet including a grasping section configured to firmly grasp the suture between the confronting surfaces in the closed position of the jaws, and an enlarged section communicating with the grasping section and configured to permit movement of the suture therein in the closed position of the jaws.

According to another aspect of the present invention, there is provided a suture manipulating instrument, comprising: first and second handles manually movable relative to each other to open and closed positions; an elongated shaft having a proximal end fixed to the first handle, and a distal end defining a first jaw engageable with a suture to be manipulated; a second jaw movably mounted to the distal end of the elongated shaft to open and closed positions with respect to the first jaw; and a coupling between the second handle and the second jaw for moving the second jaw to its open and closed positions with respect to the first jaw upon the movement of the second handle to open and closed positions with respect to the first handle; the first and second jaws being formed with confronting surfaces configured to firmly grasp a suture between them in the closed position of the second jaw with respect to the first jaw; the surface of the distal end of said first jaw opposite to its surface confronting the second jaw being outwardly curved away from the axis of said shaft to define an outer surface of convex configuration and an opposite surface of concave configuration, the distal end of the first jaw terminating in a tip of a helical configuration, and being tapered towards its distal tip such as to define a piercing tip facing away from the axis of said shaft, for piercing tissue, and for advancing said confronting surface through the pierced tissue, by rotating said elongated shaft about its axis.

Preferably, the enlarged section of the eyelet is on the distal side of the grasping section.

Two embodiments of the invention are described below for purposes of example. In one described preferred embodiment, the second jaw is pivotally mounted to the distal end of the elongated shaft about a pivotal axis perpendicular to the axis of the elongated shaft to open and closed positions with respect to the first jaw. In the second described preferred embodiment, the second jaw is rotatably mounted to the distal end of the elongated shaft about a rotary axis parallel to the axis of the elongated shaft to open and closed positions with respect to the first jaw.

Preferably, the confronting surface of the second jaw is formed with a hook formation for catching a suture, in the open position of the second jaw, and for drawing the suture towards the confronting surface of the first jaw during the movement of the second jaw to its closed position with respect to the first jaw.

According to a further feature in the described preferred embodiments, the outer surface of the second jaw conforms to the outer surface of the first jaw to serve as a smooth continuation thereof in the closed position of the jaws.

As will be described more particularly below, a suture manipulating instrument constructed in accordance with the foregoing features greatly facilitates the manipulation of sutures via endoscopes in various types of minimally invasive surgical operations.

Further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF PREFERRED
EMBODIMENTS OF THE INVENTION

Figure 1:
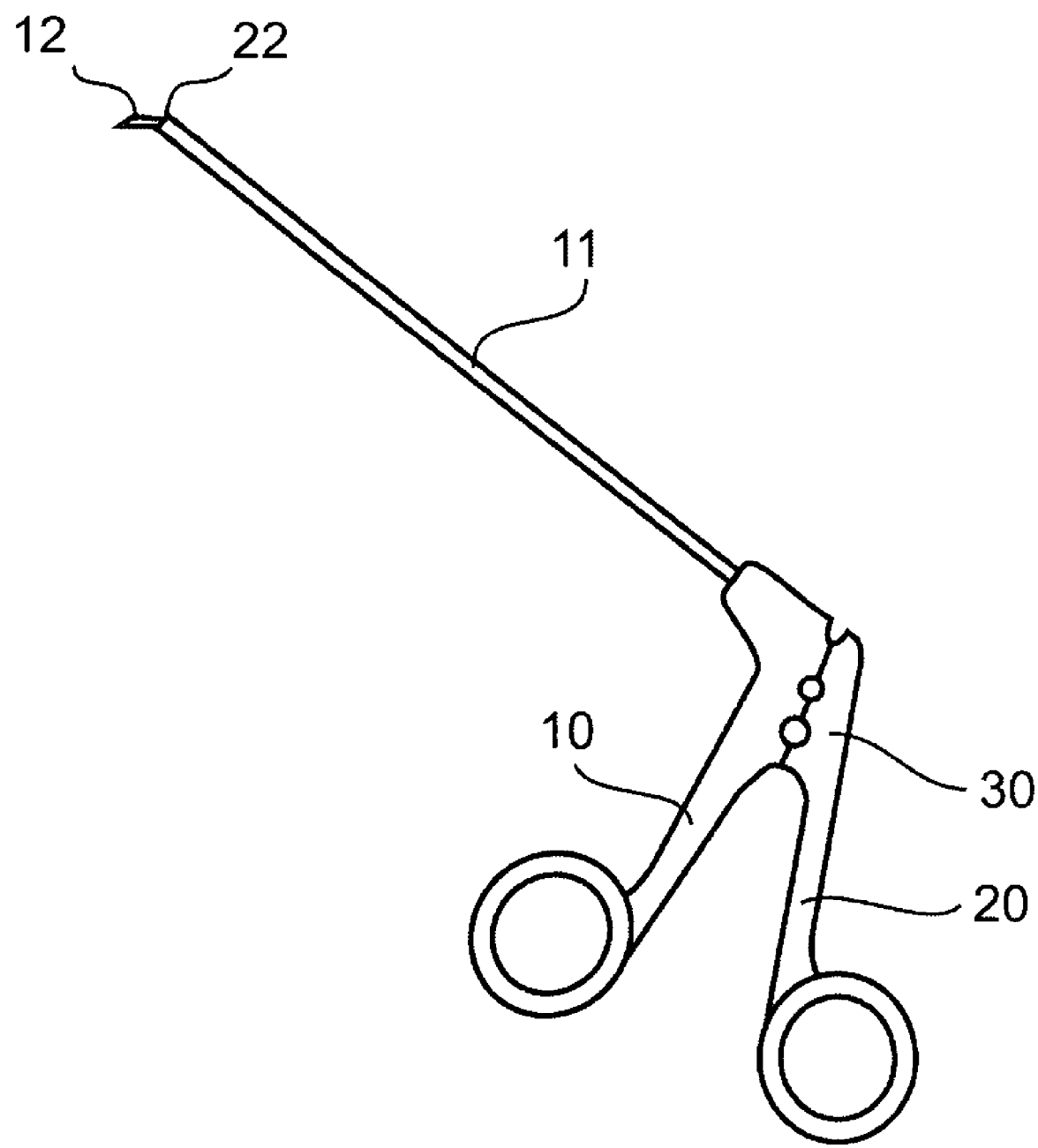
FIG. 1 illustrates one form of suture manipulating instrument constructed in accordance with the present invention.

The suture manipulating instrument illustrated in the drawings is particularly useful for internal suturing via an endoscope (not shown). As seen in FIG. 1, the illustrated instrument includes a first handle 10 and a second handle 20 pivotally mounted together by a pin 30 to open and closed positions when the two handles are engaged by the fingers of a user of the instrument.

Figure 2:
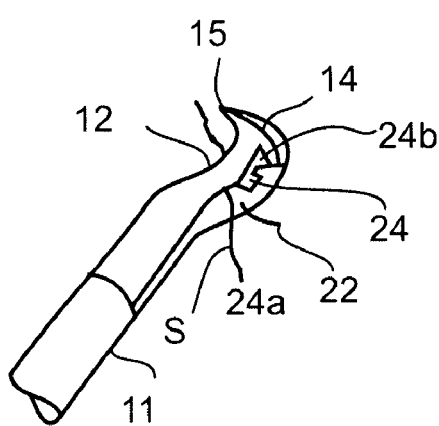
FIG. 2 is a fragmentary view illustrating the distal portion of the instrument, showing the two jaws in their closed positions.

Handle 10 carried an elongated shaft 11 having a proximal end fixed to handle 10, and a distal end defining a first jaw 12. Handle 20 is coupled via a coupling rod 21 (FIG. 3) to a second jaw 22 pivotally mounted at the distal end of elongated shaft 11 via a pin 31. The arrangement is such that pivoting handle 20 to closed and open positions with respect to handle 10 pivots jaw 22 to closed and open positions with respect to jaw 12. FIG. 2 illustrates the closed position of jaw 22 with respect to jaw 12, whereas FIG. 3 illustrates the open position of the two jaws.

Figures 3, 4:
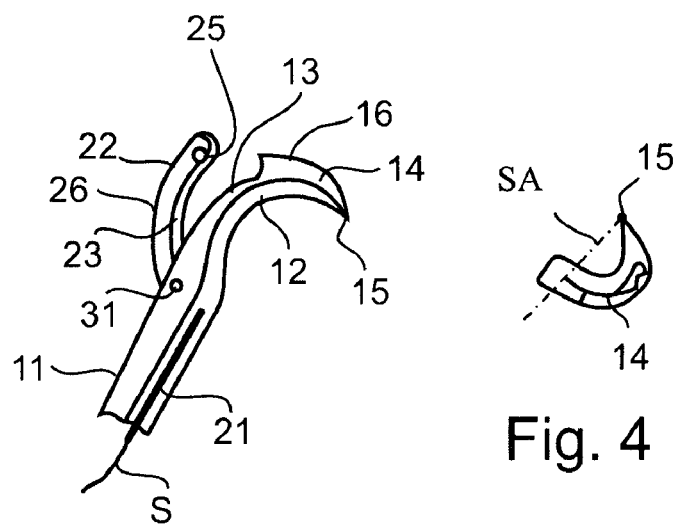
FIG. 3 is a fragmentary view illustrating the distal portion of the instrument showing the two jaws in their open position.
FIG. 4 more particularly illustrates the fixed jaw of the instrument.
Figure 5:
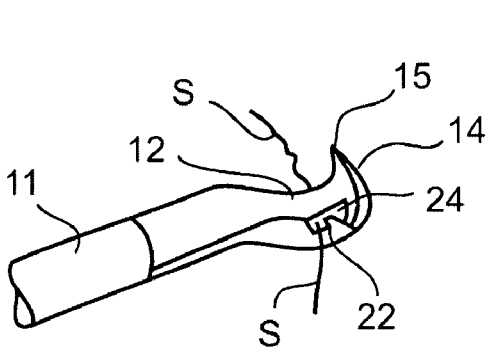
FIG. 5 illustrates the distal portion of the instrument showing the two jaws in their closed positions and the suture received within the eyelet defined by the confronting surfaces of the two jaws.
Figure 6:
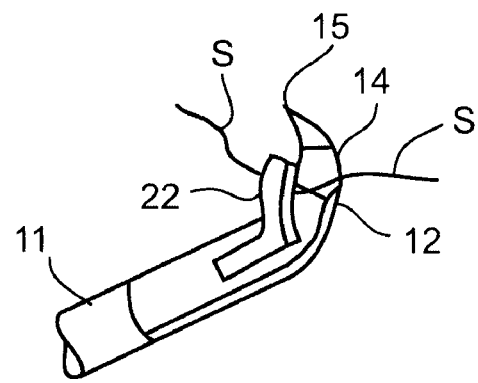
FIG. 6 illustrates the distal portion of the instrument with the two jaws in their open positions for receiving or removing the suture within the defined eyelet.

As shown particularly in FIG. 3, the two jaws, 12, 22 are formed with confronting surfaces 13, 23, respectively, which are shaped so as to define, in the closed positions of the two jaws, an eyelet 24 (FIG. 2) for receiving a suture (S, FIGS. 2, 5) to be manipulated by the instrument. Eyelet 24 includes a grasping section 24a configured to firmly grasp the suture between the two jaws in the closed position of the jaws, and an enlarged section 24b communicating with the grasping section and configured, to permit movement of the suture within the eyelet in the closed position of the jaws. FIG. 2 illustrates the suture S within the grasping section 24a of eyelet 24, whereas FIG. 5 illustrates the suture S within the enlarged section 24b of the eyelet. It will be seen that in the illustrated construction, the enlarged section 24b of the eyelet is on the distal side of the grasping section 24a.

The distal end of jaw 12 carried by the elongated shaft 11 is outwardly curved away from the axis of the shaft to define an outer surface of convex configuration and an opposite surface of concave configuration, the distal end of the first jaw terminating in a tip of a helical configuration, as shown at 14. Jaw 12 is also tapered towards its distal tip such as to define a piercing point or tip 15 for piercing tissue by rotating the shaft about its axis, shown at SA in FIG. 4. As will be described more particularly below, the helical configuration of the distal end 14 of jaw 12, terminating in its piercing tip 15, enable the user (surgeon) also to use the instrument for piercing tissue, as well as for manipulating a suture, during a surgical operation.

As shown particularly in FIG. 3, the inner surface of movable jaw 22 is formed with a hook formation 25 for catching a suture in the open position of the jaw. Hook formation 25 also enables the suture to be drawn towards the confronting recessed surfaces 13 of two jaw 12, during the movement of jaw 22 to its closed position with respect to jaw 12. The outer surface 16 of jaw 12 is curved. The outer surface 26 of jaw 22 is similarly curved so as to conform to the outer surface 16 of jaw 12, and thereby to serve as a smooth continuation of surface 16, in the closed position of jaw 22.

Following are examples of several manners of use of the described instrument during a surgical operation.

Thus, the instrument may be used to apply a new strand of suture and to pass it through tissue. This may be done by placing a suture within grasping section 24a of eyelet 24, in the closed position of the two jaws 12, 22, and then passing the instrument, with the suture firmly held between the two closed jaws, through the endoscope to one side of the tissue, until the sharp tip 15 of jaw 12 is located in alignment with the tissue to be sutured. The two grasped handles 10, 20, are then rotated together about the axis SA (FIG. 4) of elongated shaft 11 to cause tip 15 of jaw 12 to pierce the tissue and to pass through it with the suture carried between the surfaces of the eyelet grasping section 24a. When the suture exits at the opposite side of the tissue, jaws 12, 22 are opened to release the suture, or the jaws may be moved slightly apart in order to permit the suture to be passed to the enlarged eyelet section 24b for further manipulating the suture. When the suture has been released from between the two jaws, the jaws can then again be closed, and the instrument may then be rotated in the opposite direction to withdraw the two jaws from the tissue, leaving the suture threaded through the tissue.

The described instrument may also be used to catch a suture located on one side of a tissue layer and to pass it through the tissue. When the instrument is so used, the two jaws 12, 22 are closed and introduced through the endoscope to the side of the tissue opposite the suture. With the jaws 12, 22 closed, the tissue is then pierced near the suture by rotating elongated shaft 11, whereupon the jaws are opened to enable the suture to be drawn between the two surfaces 13, 23 of jaws 12, 22. The two jaws would then be closed with the suture firmly grasped by grasping section 24a of the eyelet. Elongated shaft 11 would then be rotated in the opposite direction, to thread the suture through the tissue to the other side. The suture may then be released by opening the eyelet 24. The suture may also be passed through the tissue again to form an adjacent stitch, or with the eyelet kept closed, it may be brought through the endoscope to the outside.

It will be seen that, in the instrument illustrated in FIGS. 1-6, the movable jaw (jaw 22) is a pivotal jaw, being pivotal about an axis 31 (FIG. 3), perpendicular to the axis (SA) of the elongated shaft 11.

Figure 7:
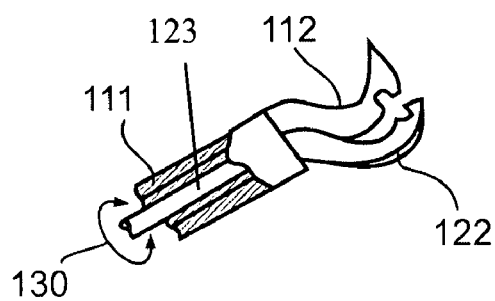
FIG. 7 illustrates a modification in the construction of the distal portion of the instrument wherein the movable jaw is rotatably mounted with respect to the fixed jaw.

FIG. 7 illustrates an alternative construction that may be used at the distal end of the jaw. The instrument illustrated in FIG. 7 also includes an elongated shaft 111 terminating at its distal end in a fixed jaw 112. In this case, however, the movable jaw 122 is rotatably mounted to its open and closed positions with respect to the fixed jaw 112 about a rotary axis parallel to the axis of the elongated shaft 111, as shown by arrow 130 in FIG. 7. For this purpose, rotary jaw 122 is carried at the distal end of a rotary rod 123 passing through the elongated shaft 111. The opposite end of rotary rod 123 could be coupled to handle 20, FIG. 1, in any suitable manner, such as by the provision of rack and pinion (not shown), for converting the pivotal movement of the handle to a rotary movement of the rod 123, and thereby a rotary movement of the jaw 122 to its open and closed positions with respect to jaw 112.

In all other respects, the instrument illustrated in FIG. 7 may be constructed and used in substantially the same manner as described above with respect to FIGS. 1-6.

It will thus be seen that the invention permits instruments to be constructed for manipulating a suture via an endoscope to provide a number of important advantages. Thus, the versatility of the described instrument allows it to perform all suturing functions in most endoscopic procedures. The helical shape of the tissue piercing element 14 enables the surgeon to pierce tissue at an obtuse angle to the axis of approach. The helical section 14 is offset from the centerline of the elongated shaft 11 and, therefore, the useful radius of curvature can be as large as the endoscope permits; a larger radius means that thicker tissue can be sutured with the instrument. Placing the eyelet 24 at the distal end of the instrument enables the suture to be easily accessible in all locations, including those within joints, which cannot be reached, or are difficult to reach, by prior art devices.

While the invention has been described with respect to two preferred embodiments, it will be appreciated that these are set forth merely for purposes of example, and that many other variations, modifications and applications of the invention may be made.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A suture manipulating instrument, comprising:
   first and second handles manually movable relative to each other to open and closed positions;
   an elongated shaft having a proximal end fixed to said first handle, and a distal end defining a first jaw engageable with a suture to be manipulated;
   a second jaw movably mounted to said distal end of said elongated shaft to open and closed positions with respect to said first jaw; and
   a coupling between said second handle and said second jaw for moving said second jaw to its open and closed positions with respect to said first jaw upon the movement of said second handle to open and closed positions with respect to said first handle;
   said first and second jaws being formed with confronting surfaces configured to firmly grasp a suture between them in the closed position of said second jaw with respect to said first jaw;
   the entire surface of the distal end of said first jaw opposite to its surface confronting the second jaw being outwardly curved away from the axis of said shaft according to a helical configuration, and being tapered towards its distal tip such as to define a sharp piercing tip facing away from the axis of said shaft, for piercing tissue, and for advancing said piercing tip through the pierced tissue with the suture caught between said confronting surfaces of the closed jaws before or after the tissue is pierced, by rotating said elongated shaft about its axis.

2. The instrument according to claim 1, wherein:
   the distal end of said first jaw has an inner surface proximal to the axis of said shaft and an outer surface remote from the axis of said shaft;
   said second jaw is movably mounted to said outer surface of said first jaw so as to define therewith said confronting surfaces for firmly grasping the suture; and
   said confronting surfaces of said first and second jaws define, in the closed position of said jaws, an eyelet for receiving a suture; said eyelet including a grasping section configured to firmly grasp the suture between said confronting surfaces in the closed position of said jaws, and an enlarged section communicating with said grasping section and configured to permit movement of the suture therein in the closed position of said jaws.

3. The instrument according to claim 2, wherein said enlarged section of the eyelet is on the distal side of said grasping section.

4. The instrument according to claim 1, wherein said second jaw is pivotally mounted to said distal end of the elongated shaft about a pivotal axis perpendicular to the axis of said elongated shaft to open and closed positions with respect to said first jaw.

5. The instrument according to claim 1, wherein said second jaw is rotatably mounted to said distal end of the elongated shaft about a rotary axis parallel to the axis of said elongated shaft to open and closed positions with respect to said first jaw.

6. The instrument according to claim 1, wherein said confronting surface of said second jaw is formed with a hook formation for catching a suture, in the open position of said second jaw, and for drawing the suture towards said confronting surface of the first jaw during the movement of said second jaw to its closed position with respect to said first jaw.

7. The instrument according to claim 1, wherein the outer surface of said second jaw conforms to the outer surface of said first jaw to serve as a smooth continuation thereof in the closed position of said jaws.

8. The instrument according to claim 1, wherein said first and second jaws are pivotally mounted with respect to each other.

9. The instrument according to claim 1, wherein said second jaw is coupled to said second handle by a rod passing through said elongated shaft.

10. The instrument according to claim 1 wherein the second jaw is outwardly curved away from the axis of said shaft to define an inner confronting surface of concave configuration, and an outer non-confronting surface of convex configuration.

11. An instrument according to claim 1, wherein said helical configuration has an axis offset from the centerline of the elongated shaft to allow for piercing the tissue by rotating said elongate shaft about its axis.

12. A suture manipulating instrument, comprising:
an elongated shaft having a distal end defining a first jaw engageable with a suture to be manipulated;
a second jaw movably mounted to said distal end of said elongated shaft movable to open and closed positions with respect to said first jaw; and
a coupling for moving said second jaw to its open and closed positions with respect to said first jaw;
said first and second jaws being configured to capture a suture between them in the closed position of said second jaw with respect to said first jaw;
wherein the entire surface of the distal end of said first jaw, opposite to its surface confronting the second jaw, is curved according to a helical configuration and is tapered towards its distal tip such as to define a piercing tip; and wherein said helical configuration has an axis offset from the centerline of the elongated shaft to allow for piercing the tissue by rotating said elongated shaft about its axis and for advancing a suture, captured between the closed jaws before or after the tissue is pieced, through the tissue.

13. The instrument according to claim 12, wherein said first and second jaws define, in the closed position of said jaws, an eyelet for receiving a suture; said eyelet including a grasping section configured to grasp the suture between said jaws in the closed position of said jaws, and an enlarged section communicating with said grasping section and configured to permit movement of the suture therein in the closed position of said jaws.

14. The instrument according to claim 13, wherein said enlarged section of the eyelet is on the distal side of said grasping section.

15. The instrument according to claim 12, wherein said second jaw is pivotally mounted to said distal end of the elongated shaft about a pivotal axis perpendicular to the axis of said elongated shaft to provide open and closed positions with respect to said first jaw.

16. The instrument according to claim 12, wherein said second jaw is rotatably mounted to said distal end of the elongated shaft about a rotary axis parallel to the axis of said elongated shaft to provide open and closed positions with respect to said first jaw.

17. The instrument according to claim 12, wherein said first and second jaws have confronting surfaces which mate in a closed position and wherein said confronting surface of said second jaw is formed with a hook formation for catching a suture, in the open position of said second jaw, and for drawing the suture towards said conforming surface of the first jaw during the movement of said second jaw to its closed position with respect to said first jaw.

18. The instrument according to claim 12, wherein the outer surface of said second jaw conforms to the outer surface of said first jaw to serve as a smooth continuation thereof in the closed position of said jaws.

19. The instrument according to claim 12, wherein said first and second jaws are pivotally mounted with respect to each other.

20. The instrument according to claim 12, wherein said second jaw is coupled to a rod passing through said elongated shaft.

* * * * *